United States Patent
Dhuppad et al.

(10) Patent No.: US 8,673,356 B2
(45) Date of Patent: Mar. 18, 2014

(54) STABLE FIXED DOSE TOPICAL FORMULATION

(75) Inventors: Ulhas Rameshchandra Dhuppad, Nashik (IN); Nitin Babulal Bhamre, Nashik (IN); Sunil Sudhakar Chaudhari, Nashik (IN); Girish Ramakrishna Trivedi, Nashik (IN); Akhilesh Dayanand Sharma, Mumbai (IN); Prashant Dongre, Mumbai (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 0 days.

(21) Appl. No.: 12/404,462

(22) Filed: Mar. 16, 2009

(65) Prior Publication Data

US 2010/0068284 A1 Mar. 18, 2010

Related U.S. Application Data

(60) Provisional application No. 61/042,142, filed on Apr. 3, 2008, provisional application No. 61/141,175, filed on Dec. 29, 2008.

(30) Foreign Application Priority Data

Mar. 17, 2008 (IN) ............................ 532/MUM/2008
Dec. 10, 2008 (IN) .......................... 2570/MUM/2008

(51) Int. Cl.
*A61K 8/63* (2006.01)
*A61K 8/368* (2006.01)
*A61K 9/50* (2006.01)
*A61Q 19/00* (2006.01)
*C07H 15/16* (2006.01)

(52) U.S. Cl.
USPC .................... 424/489; 424/78.02; 424/78.07; 424/404; 514/422; 514/859

(58) Field of Classification Search
None
See application file for complete search history.

(56) References Cited

U.S. PATENT DOCUMENTS 5,955,109 A * 9/1999 Won et al. ...................... 424/501
2002/0176891 A1 * 11/2002 Dow et al. ..................... 424/487

FOREIGN PATENT DOCUMENTS

| EP | 22652268 | | 9/2009 |
| WO | 2006/048747 A1 | | 5/2006 |
| WO | WO 2006048747 A1 | * | 5/2006 |

OTHER PUBLICATIONS

EG de Jalon, MJ Blanco-Prieto, P Ygartua, S Santoyo. "PLGA microparticles: possible vehicles for topical drug delivery." International Journal of Pharmaceutics, vol. 226, 2001, pp. 181-184.*
Retin-A Micro (trentoin) Gel. http://dailymed.nlm.nih.gov/dailymed/archives/fdaDrugInfo.cfm?archiveid=2366 (accessed Mar. 18, 2011). 15 total pages. Oct. 2006 (see last page for date).*
Gollnick H et al., Management of Acne., Journal of the American Academy of Dermatology, Jul. 2003, pp. S1-2, vol. 49, Issue 1, Part 2, Elsevier.
E.G. De Jalon et.al, PLGA microparticles: possible vehicles for topical drug delivery, International Journal of Pharmaceutics, Sep. 11, 2001, 181-184, vol. 226, Issues 1-2, Elsevier.
Retin-A-micro (http://dailymed.nim.nih.gov/archives/fdaDrugInfo.cfm?archiveid=2366 Oct. 2006).
Rolland et al., Site-Specific Drug Delivery to Pilosebaceous Structures Using Polymeric Microspheres. Pharmaceutical Research, vol. 10, No. 12, 1993 pp. 1738-1744.

* cited by examiner

Primary Examiner — Frederick Krass
Assistant Examiner — Isaac Shomer
(74) Attorney, Agent, or Firm — Blank Rome LLP

(57) ABSTRACT

The present invention relates to stable fixed dose topical formulations comprising an antiacne agent and an antibiotic, which exhibit storage stability at a temperature of about 40° C. and relative humidity of about 75% for a period of at least 3 months. Particularly, the present invention relates to stable fixed dose topical formulations comprising therapeutically effective amounts of (a) adapalene-containing microspheres and (b) clindamycin, a process for their preparation thereof and their use for the treatment of acne.

9 Claims, No Drawings

STABLE FIXED DOSE TOPICAL FORMULATION

PRIORITY

This application claims priority to Indian Provisional Patent Applications 532/MUM/2008 (filed on Mar. 17, 2008) and 2570/MUM/2008 (filed on Dec. 10, 2008), and under 35 U.S.C. §119(e) to U.S. Provisional Applications 61/042,142 (filed on Apr. 3, 2008) and 61/141,175 (filed on Dec. 29, 2008), the contents of each of which are incorporated by reference herein.

BACKGROUND OF THE INVENTION

1. Technical Field

The present patent application relates to a stable fixed dose topical formulation comprising an anti-acne agent and an antibiotic, wherein the anti-acne agent is contained in microspheres. Particularly, the present patent application relates to a stable fixed dose topical formulation comprising therapeutically effective amounts of (a) adapalene-containing microspheres and (b) clindamycin, their use for the treatment of acne, and a process for preparing the same.

2. Description of the Related Art

Acne vulgaris is an inflammatory disease of the sebaceous glands characterized by an eruption of the skin, often pustular in nature but not suppurative. Acne vulgaris is a skin condition that affects over 85% of adolescents and young adults. The following are four primary factors that are believed to lead to the formation of acne vulgaris: (1) increased sebum output resulting in oily, greasy skin; (2) increased bacterial activity normally due to an overabundance of *propionibacterium acnes*; (3) plugging (hypercornification) of the follicle or pilosebaceous duct; and (4) inflammation caused by substances leaking into the dermis. The major physical ramification of acne is the appearance of lesions on the face, chest and/or back areas. Acne lesions change over time from blackheads and whiteheads to inflammatory lesions (papules and pustules) that upon healing may leave pigmentary changes, cysts, or scars. Acne often results in unsightly lesions, particularly on the face, and in some cases may even cause severe scarring.

An effective antiacne therapy should prevent acne recurrence by targeting the early stages of comedogenesis and the precursor of mature acne lesions, the microcomedo. There are a variety of methods for treating acne vulgaris such as, for example, administering various agents either orally or topically to the skin. Nevertheless, acne vulgaris is seldom cured and only can be controlled with difficulty. In no case has a treatment designed for any of the aforementioned causes proven to be uniformly effective. Recently published guidelines recommend topical retinoids with or without benzoyl peroxide for maintenance following initial combination treatment with an antimicrobial. (See, Gollnick H et. al., *J Am Acad Dermatol.* 2003; 49 (1), S1-S38).

Adapalene, chemically (6-[3-(1-adamantyl)-4-methoxyphenyl]-2-naphthoic acid), is an antiacne agent indicated for the topical treatment of acne vulgaris. It is a white to off-white powder, which is soluble in tetrahydrofuran, very slightly soluble in ethanol, and practically insoluble in water. The molecular formula is $C_{28}H_{28}O_3$ and molecular weight is 412.53. Adapalene is represented by the following structural formula.

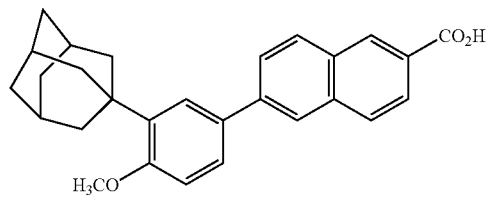 [SMILES: COc1ccc(-c2ccc3cc(C(=O)O)ccc3c2)cc1C12CC3CC(CC(C3)C1)C2]

Clindamycin, an antibiotic of the lincosamide class, is often used in topical preparations for acne treatment. Clindamycin phosphate is a water soluble ester of the semisynthetic antibiotic produced by a 7(S)-chloro-substitution of the 7(R)-hydroxyl group of the parent antibiotic lincomycin. and has the structural formula represented below:

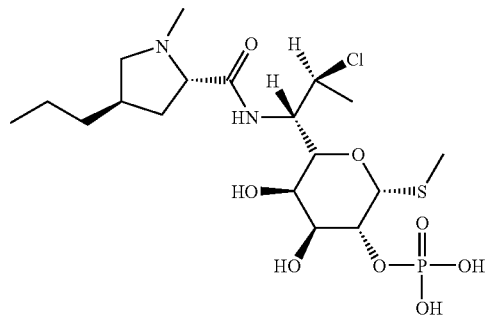

The chemical name for clindamycin phosphate is methyl 7-chloro-6,7,8-trideoxy-6-(1-methyl-trans-4-propyl-L-2-pyrrolidinecarboxamido)-1-thio-L-threo-D-galactooctopyranoside 2-(dihydrogen phosphate). Although clindamycin phosphate is inactive in vitro, rapid in vivo hydrolysis converts this compound to the antibacterially active clindamycin.

Co-assigned PCT Application Publication No. WO 2006/048747, which describes topical pharmaceutical compositions containing an antiacne compound and antibiotic compound and co-assigned Indian patent application No. 805/MUM/2004 drawn to adapalene microsphere pharmaceutical compositions, are incorporated herein by reference in their entirety.

SUMMARY OF THE INVENTION

The present invention relates to a stable fixed dose topical formulation comprising a therapeutically effective amount of (a) adapalene and (b) clindamycin; wherein the adapalene is contained in microspheres.

In an embodiment, the present invention provides a stable topical formulation, comprising therapeutically effective amounts of (a) adapalene-containing microspheres and (b) clindamycin, characterized by stability at pH values in the range of about 5.0 to about 6.4.

In another embodiment, the present invention provides a stable topical formulation, comprising therapeutically effective amounts of (a) adapalene-containing microspheres and (b) clindamycin, characterized by stability at pH values in the range of about 5.4 to about 6.2.

In an embodiment, the present invention provides microspheres in the stable fixed dose topical formulation, wherein the microspheres are composed of a pharmaceutically acceptable polymer having a mean particle size ranging from about 2 μm to about 30 μm, In an embodiment, the present invention provides microspheres in the stable fixed dose topical formulation, wherein the microspheres are composed of a pharmaceutically acceptable polymer having a mean particle size ranging from about 5 μm to about 20 μm.

In an embodiment, the present invention provides microspheres in the stable fixed dose topical formulation, wherein the microspheres are composed of a pharmaceutically acceptable polymer having a mean particle size ranging from about 5 μm to about 15 μm.

The present invention provides microspheres in the stable fixed dose topical formulation, wherein the weight ratio of adapalene to the microspheres ranges from about 1:1 to about 1:20.

The present invention provides microspheres in the stable fixed dose topical formulation, wherein the weight ratio of adapalene to the microspheres ranges from about 1:5 to about 1:15.

The present invention provides microspheres in the stable fixed dose topical formulation, wherein the weight ratio of adapalene to the microspheres ranges from about 1:8 to about 1:10.

In another embodiment of the present invention microspheres in the stable fixed dose topical formulation, wherein the weight ratio of adapalene to clindamycin in the fixed dose topical formulation ranges from about 1:1 to about 1:30.

In another embodiment of the present invention microspheres in the stable fixed dose topical formulation, wherein the weight ratio of adapalene to clindamycin in the fixed dose topical formulation ranges from about 1:5 to about 1:15.

The present invention provides the formulation, as described, comprises about 0.1% w/w of adapalene and about 1.0% w/w of clindamycin (based on 100% total weight of the formulation).

In a specific embodiment, the present invention provides a stable fixed dose topical gel formulation comprising by weight (a) 0.1% of adapalene; (b) 1.0% of clindamycin; and (c) a gelling agent; wherein the adapalene is contained in microspheres.

In another embodiment, the present invention provides a stable fixed dose topical aqueous gel formulation comprising by weight (a) 0.1% of adapalene; (b) 1.0% clindamycin; and (c) about 0.5% to about 1.5% carbomer as a gelling agent; wherein the adapalene is contained in microspheres.

In yet another embodiment, the present invention provides a stable fixed dose topical aqueous gel formulation comprising by weight (a) 0.1% of adapalene; (b) 1.0% clindamycin; (c) about 0.5% to about 1.5% carbomer as a gelling agent; and (d) propylene glycol; wherein the adapalene is contained in microspheres.

In another embodiment, the present invention provides fixed dose topical formulations comprising therapeutically effective amounts of (a) adapalene-containing microspheres and (b) clindamycin possessing a storage stability at accelerated conditions for a period of at least 3 months, or at least 2 months, or at least 1 month, wherein the accelerated conditions are at a temperature of about 40° C. and a relative humidity of about 75%.

In still another embodiment, the present invention provides stable topical formulations, comprising therapeutically effective amounts of (a) adapalene-containing microspheres and (b) clindamycin, with stability at pH values in the range of 5 to 6.5; preferably 5.4 to 6.2, further characterized by an efficacy test at 12 weeks, relative to topical formulations comprising adapalene with clindamycin.

In still another embodiment, the present invention provides stable topical formulations, comprising therapeutically effective amounts of (a) adapalene-containing microspheres and (b) clindamycin, with stability at pH values in the range of 5 to 6.4; preferably 5.4 to 6.2, further characterized by an efficacy test at 12 weeks, relative to topical formulations comprising adapalene alone and/or adapalene in microsphere.

The present invention provides the process for the preparation of the adapalene-containing microspheres, comprising: dissolving adapalene in a solvent system; dispersing the microspheres into the adapalene solution; then removing the solvent.

In an embodiment, the present invention provides a process for the preparation of stable fixed dose topical formulations, described herein, comprising:

(a) dissolving adapalene in a solvent system, mixing the adapalene solution with microspheres, and removing the solvent; and (b) combining the adapalene-containing microspheres with clindamycin and further with ancillary excipients into stable fixed dose topical formulations in the form of a gel, lotion, paste, dispersion, ointment or cream.

In another embodiment, the present invention provides a method for treating acne (e.g., acne vulgaris) in a mammal (e.g., a human) in need thereof comprising applying to the afflicted skin region of the mammal the stable fixed dose topical formulation comprising therapeutically effective amounts of (a) adapalene-containing microspheres; and (b) clindamycin.

In yet another embodiment, the present invention provides a method for inhibiting the recurrence of acne (e.g., acne vulgaris) in a mammal (e.g., a human) in which the clinical condition associated with the acne has been alleviated. This method comprises topically applying to the afflicted skin region of the mammal the stable fixed dose topical formulation comprising therapeutically effective amounts of (a) adapalene-containing microspheres; and (b) clindamycin.

Still, in yet another embodiment, the present invention provides a method of (i) treating mammals afflicted with acne (e.g., acne vulgaris) and inhibiting its recurrence, or (ii) inhibiting or preventing the recurrence of acne (e.g., acne vulgaris), which comprises, topically applying to the afflicted skin region of the mammal, therapeutically effective amounts of (a) adapalene-containing microspheres; and (b) clindamycin on a regular basis (e.g., once daily) for at least 12 weeks. The topical formulation can be in the form of a gel, lotion, paste, dispersion, ointment or cream.

DETAILED DESCRIPTION OF THE INVENTION

The definitions of the terms used herein follow. However, where a definition set forth in the present application relative to one in an earlier provisional application (from which the priority is claimed) are in conflict, the definition in the present application shall control the meaning of the term(s).

The term "acne" includes inflammatory diseases of the pilosebaceous follicles and/or skin glands, and commonly is characterized by papules, pustules, cysts, nodules, comedones, other blemishes or skin lesions. The term "acne" as used herein includes all known types of acne. Some types of acne which can be treated with the topical composition of the present invention are, for example, acne vulgaris, acne comedo, papular acne, premenstrual acne, preadolescent acne, acne venenata, acne cosmetica, pomade acne, acne detergicans, acne excoriee, gram negative acne, pseudofolliculitis barbae, folliculitis, perioral dermatitis, hiddradenitis suppurativa, cystic acne, acne atrophica, bromide acne, chlorine acne, acne conglobata, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea.

The term "active ingredient" (used interchangeably with "active" or "active agent") as used herein includes adapalene and clindamycin and their pharmaceutically acceptable salts, esters or any other derivatives. For example, the term "clindamycin" also includes its pharmaceutically acceptable salt or ester such as, but not limited to, clindamycin hydrochloride, clindamycin phosphate, clindamycin palmitate, and clindamycin palmitate hydrochloride.

The terms "effective amount" or "therapeutically effective amount" denotes an amount of an active ingredient that, when administered to a subject for treating a state, disorder or condition, produces an intended therapeutic benefit in a subject. The effective amount will vary depending on the active ingredient, the disease and its severity, and the age, weight, physical condition and responsiveness of the mammal to be treated.

The term "gelling agent" is synonymous with viscosifying agent, and refers to an agent that increases the viscosity of the formulation, for example, by forming a crosslinking structure. Such agents include, by way of example and without limitation, carbomers (CARBOPOL®), cellulosic polymers, naturally-occurring, synthetic or semisynthetic gums (such as xanthan gum, acacia and tragacanth), sodium alginate, gelatin, modified starches, cellulosic polymers (such as hydroxypropyl cellulose, hydroxyethyl cellulose, hydroxypropyl methylcellulose, hydroxypropyl methylcellulose phthalate, and methyl cellulose), co-polymers (such as those formed between maleic anhydride and methyl vinyl ether), colloidal silica, methacrylate derivatives, polyethylene oxides, polyoxyethylene-polyoxypropylene copolymers, polyvinyl alcohol and mixtures thereof. Preferably, the gelling agent in the context of present invention is carbomer.

The terms, "adapalene-containing microspheres", "microspheres containing adapalene", "adapalene contained in microspheres", "microsphere adapalene" and "adapalene microspheres" are synonymous and interchangeably used herein.

The term "infuse" as used herein means that the particles of one substance mixes intimately with the mass of another; where the degree of mixing is relative to the ratios therewith. The terms, "adapalene-infused microspheres", "microspheres infused with adapalene", "microsphere adapalene" and "adapalene microspheres" are synonymous and interchangeably used herein.

The term "irritation" or "irritation potential" or "irritate" or "irritating" as used herein refers to that portion of the skin exhibiting a symptom either characterized by burning, erythema and/or pruritis. Without being bound by any particular theory, it is believed that the formulation of the invention preferentially delivers the active agent to its site of action, the sebaceous gland, on the skin surface, thereby resulting in the enhanced anti-acne efficacy and reduced irritation when applied topically.

The term "pharmaceutically acceptable" such as in the recitation of a "pharmaceutically acceptable carrier" or a "pharmaceutically acceptable derivative" refers to compounds and compositions that are physiologically tolerable and do not typically produce untoward reactions when administered to an animal (e.g., a human). The term "pharmaceutically acceptable" as used in connection with components includes those components approved by a regulatory agency of the Federal or a state government or listed in the U.S. Pharmacopeia or other generally recognized pharmacopeia for use in mammals, such as humans.

The term "recurrence" in relation to acne described herein refers to 50% or more increase in the number of total lesions (including inflammatory as well as non-inflammatory lesions) following the acne treatment using the fixed dose topical formulation of the present invention for a period of at least 12 weeks, wherein the incidence of such recurrence is monitored for a period of 3 months after the 12 weeks' acne treatment.

The term "subject" or "patient" refers to a mammal, and preferably a human.

The terms "topical formulation" and "topical composition" are used herein to refer to a pharmaceutical composition that is intended for topical (or local) application to the affected skin or mucosa regions of the mammal. Such a topical formulation can be, for example, in the form of a gel, lotion, paste, dispersion, ointment or cream.

For the topical formulation being referred to as "stable" in the context of present invention, the formulation should contain not more than 9.0% w/w of clindamycin base impurity and not more than 8.0% w/w of total impurities (excluding the clindamycin base) related to clindamycin (based on 100% weight of the formulation) when stored at accelerated conditions (i.e., at a temperature of about 40° C. and relative humidity of about 75%) for a period of at least 3 months, or at least 2 months, or at least 1 month. Moreover, for a stable fixed dose topical formulation, it is necessary to maintain the pH of the formulation in the range of about 5.0 to about 6.4; preferably from about 5.4 to about 6.2. This pH range has been found to be critical for maintaining the stability of the topical formulation. For example, in the context of present formulation, at pH<5.0, the clindamycin base impurity increases to unacceptable levels, whereas at pH>6.4, the total impurities (excluding clindamycin base) increase to very high levels when said formulation is stored at accelerated conditions for 3 months.

Ointments are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency. As with other carriers or vehicles, an ointment base should be inert, stable, nonirritating and nonsensitizing. As explained in *Remington: The Science and Practice of Pharmacy*, 19th Ed. (Easton, Pa.: Mack Publishing Co., 1995), at pages 1399-1404, ointment bases may be grouped in four classes: oleaginous bases; emulsifiable-bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

Lotions, are preparations to be applied to the skin surface without friction, and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl cellulose, or the like.

Pastes are semisolid dosage forms in which the active agent is suspended in a suitable base. Depending on the nature of the base, pastes are divided between fatty pastes or those made from a single-phase aqueous gel. The base in a fatty paste is generally petrolatum or hydrophilic petrolatum or the like. The pastes made from single-phase aqueous gels generally incorporate carboxymethyl cellulose or the like as a base.

The terms "treating" or "treatment" of a state, disorder or condition as used herein means: (1) inhibiting the state, disorder or condition, i.e., arresting or reducing the development of the disease or at least one clinical or subclinical symptom thereof, or (2) relieving the disease, i.e., causing regression of the state, disorder or condition or at least one of its clinical or subclinical symptoms. The benefit to a subject to be treated is either statistically significant or at least perceptible to the patient or to the physician.

The present invention relates to a stable fixed dose topical formulation comprising therapeutically effective amounts of: (a) adapalene; and (b) an antibiotic; wherein the adapalene is contained in microspheres.

It has been found that to provide a stable fixed dose topical formulations comprising therapeutically effective amounts of adapalene-containing microspheres and clindamycin, it is necessary to maintain the pH of the formulation in the range of about 5.0 to about 6.4; preferably from about 5.4 to about 6.2. This pH range has been found to be critical for maintaining the stability of the topical formulation. For example, in the context of present formulation, at pH<5.0, the clindamycin base impurity increases to unacceptable levels, whereas at pH>6.4, the total impurities (excluding clindamycin base) increase to very high levels when said formulation is stored at accelerated conditions for 3 months. For the topical formulation being referred to as "stable" in the context of present invention, the formulation should contain not more than 9.0% w/w of clindamycin base impurity and not more than 8.0% w/w of total impurities (excluding the clindamycin base) related to clindamycin (based on 100% weight of the formulation) when stored at accelerated conditions (i.e., at a temperature of about 40° C. and relative humidity of about 75%) for a period of at least 3 months, or at least 2 months, or at least 1 month.

The present invention provides the stable topical formulations, herein described having a storage stability at accelerated conditions for a period of at least 3 months, or at least 2 months, or at least 1 month, wherein the accelerated conditions comprise temperature of about 40° C. and relative humidity of about 75%.

In still another embodiment, the present invention provides stable topical formulations, comprising therapeutically effective amounts of (a) adapalene-containing microspheres and (b) clindamycin, with stability at pH values in the range of 5.0 to 6.4; preferably 5.4 to 6.2, further characterized by an efficacy test at 12 weeks, relative to topical formulations comprising adapalene alone and/or adapalene in microsphere.

The present invention provides stable fixed dose topical formulations comprising therapeutically effective amounts of (a) adapalene-containing microspheres (b) clindamycin, possessing storage stability at accelerated conditions for a period of at least 3 months, or at least 2 months, or at least 1 month, wherein the accelerated conditions comprise temperature of about 40° C. and relative humidity of about 75%.

In an embodiment, the stable topical formulations, herein described previously contain not more than 8.5% w/w of clindamycin base impurity and not more than 7.0% w/w of total impurities (excluding the clindamycin base) related to clindamycin (based on 100% weight of the formulation) when stored at accelerated conditions (about 40° C. temperature and 75% relative humidity) for a period of 3 months.

The formulation, described herein above, comprises about 0.1% w/w of adapalene and about 1.0% w/w of clindamycin (based on 100% total weight of the formulation). According to one preferred embodiment, the formulation described herein comprises 0.01% to 0.3% w/w of adapalene and 0.5% to 5.0% w/w of clindamycin (based on 100% total weight of the formulation). More preferably, the fixed dose topical formulation contains 0.03% to 0.1% w/w of adapalene and 1.0% to 2.0% w/w of clindamycin (based on 100% total weight of the formulation). Preferably, the amounts of adapalene and clindamycin are therapeutically effective to treat acne and/or inhibit the recurrence of acne or reduce the severity of the acne recurrence in a mammal, such as a human.

The stable fixed dose topical formulation of the present invention may be an aqueous gel formulation comprising by weight (a) 0.1% of adapalene; (b) 1.0% clindamycin; and (c) about 0.5% to about 1.5% carbomer as a gelling agent; wherein the adapalene is contained in microspheres. Optionally, the stable fixed dose topical aqueous gel formulation, further comprises propylene glycol, preservative and surfactant. The amount of gelling agent varies widely and ordinarily ranges from about 0.1% to about 2.0% by weight, preferably from about 0.5% to about 1.5% by weight, based on the total weight of the formulation.

The microspheres used herein are capable of containing an active agent that is to be released after application to the skin. U.S. Pat. No. 5,955,109 (the '109 patent), incorporated herein by reference, in its entirety, discloses the preparation of and the description of microspheres as rigid, open-pore, chemically and biologically inert particles. The '109 patent discloses that materials are held inside the pores of microspheres by capillary forces. The '109 patent also describes that microspheres can have a mean particle size ranging from about 1 μm to about 100 μm, where a mean particle size of about 2 μm to about 30 μm (or even more desirably about 5 μm to about 20 μm) are preferable for topical use as they are believed to readily penetrate the sebaceous duct.

Various pharmaceutically acceptable materials can be used for the preparation of microspheres. These materials include poly(dl-lactic-co-glycolic acid), silica, cellulosic polymers, divinyl benzene and methacrylates. The microspheres are preferably methacrylate based microspheres, more preferably, methyl methacrylate copolymer, free of vinylpyridine derivative.

The microspheres have a mean particle size of about 2 μm to about 30 μm, preferably about 5 μm to about 20 μm. The weight ratio of adapalene to microspheres ranges from about 1:1 to about 1:20, or from about 1:5 to about 1:15. More preferably, the weight ratio of adapalene to the microspheres ranges from about 1:8 to about 1:10.

Still, in another embodiment, the present invention provides a process for preparing the stable fixed dose topical formulation by infusing microspheres with adapalene using a solvent system, and combining the adapalene-containing microspheres with clindamycin to subsequently obtain topical formulations in the form of a gel, lotion, paste, dispersion, ointment or cream.

The microspheres may be loaded with adapalene by dissolving adapalene in a solvent system, mixing the adapalene solution with microspheres and then removing the solvent.

The solvent or solvent system used for dissolving (or solubilizing) adapalene is selected from tetrahydrofuran; ether; petroleum ether; alcohols, e.g., methanol, ethanol, isopropyl alcohol and higher alcohols; chlorinated hydrocarbons, e.g., chloroform, carbon tetrachloride, methylene chloride and ethylene dichloride; acetates, e.g., ethyl acetate; and mixtures thereof. Preferably, the solvent is tetrahydrofuran (THF).

The solvent may be removed by any conventional method known in the art, such as distillation, spray drying, lyophilization, oven drying, fluidized bed drying, rota-evaporation using rotavapor, and their combinations. Preferably, the solvent is removed by distillation, rota-evaporation and oven drying at about 60° C. to 75° C.

The adapalene-containing microspheres may then be combined with clindamycin and further with ancillary excipients for subsequent fixed dose topical formulations in the form of a gel, lotion, paste, dispersion, ointment or cream.

The topical compositions of the present invention can further contain other pharmaceutically acceptable excipients. Suitable pharmaceutically acceptable excipients include, but are not limited to, buffering agents, surfactants, chelating agents, preservatives, polymers, and mixtures thereof. Examples of these excipients are described in, for example, Howard C. Ansel et. al., *Pharmaceutical Dosage Forms and Drug Delivery Systems*, (7th Ed. 1999); Alfonso R. Gennaro et al., *Remington: The Science and Practice of Pharmacy*, (20th Ed. 2000); and A. Kibbe, *Handbook of Pharmaceutical Excipients*, (3rd Ed. 2000), the contents of which are incorporated by reference herein.

Suitable buffering agents include, by way of example and without limitation, sodium hydroxide, potassium hydroxide, and ammonium hydroxide.

Non-limiting examples of surfactants or emulsifiers include, poloxamer, polyoxyethylene sorbitan esters (known as POLYSORBATE® or TWEEN®), polyethoxylated castor oil (CREMOPHOR®), methyl glucose sesquistearate, polyethyleneglycol (PEG)-20 methyl glucoside sesquistearate, Steareth-21, polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 glyceryl monostearate, sucrose monostearate, sucrose polystearates, polyglyceryl 10 stearate, polyglcyeryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, steareth-2, PEG-5 soya sterol oil, PEG-10 soya sterol oil, diethanolamine cetyl phosphate, sorbitan monostearate, diethylenglycol monostearate, glyceryl monostearate, and the like and mixtures thereof.

Suitable chelating agents include, but are not limited to, mild agents such as ethylenediaminetetraacetic acid (EDTA), disodium edentate, EDTA derivatives, and mixtures thereof.

Suitable preservatives include, by way of example and without limitation, phenoxyethanol, parabens (such as methylparaben and propylparaben), propylene glycols, sorbates, urea derivatives (such as diazolindinyl urea), and any combination thereof.

Suitable polymers include, by way of example and without limitation, those known in the art such as gum arabic, sodium based lignosulfonate, methyl methacrylate, methacrylate copolymers, isobutyl methacrylate, ethylene glycol dimethacrylate and mixtures thereof.

The topical composition of the present invention may further comprise emollients. Examples of such emollients include, but are not limited to, caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea and mixtures thereof.

The topical composition of the present invention may further comprise humectants. Examples of such humectants include, but are not limited to, propylene glycol, glycerin, butylene glycol, sorbitol, triacetin and mixtures thereof.

The topical composition of the present invention can further contain one or more suitable solvents. Non-limiting examples of solvents include, water; tetrahydrofuran; propylene glycol; liquid petrolatum; ether; petroleum ether; alcohols, e.g., methanol, ethanol, isopropyl alcohol and higher alcohols; aromatics, e.g., benzene and toluene; alkanes, e.g., pentane, hexane and heptane; ketones, e.g., acetone and methyl ethyl ketone; chlorinated hydrocarbons, e.g., chloroform, carbon tetrachloride, methylene chloride and ethylene dichloride; acetates, e.g., ethyl acetate; lipids, e.g., isopropyl myristate, diisopropyl adipate and mineral oil and the like and mixtures thereof.

The present invention provides a method for treating acne (e.g., acne vulgaris) in a mammal (e.g., a human) in need thereof comprising applying to the afflicted skin region of the mammal the disclosed adapalene-containing microspheres and clindamycin fixed dose topical formulation.

In yet another embodiment, the present invention provides a method of (i) treating mammals afflicted with acne (e.g., acne vulgaris) and inhibiting its recurrence, or (ii) inhibiting or preventing the recurrence of acne (e.g., acne vulgaris), which comprises, topically applying to the afflicted skin region of the mammal, therapeutically effective amounts of (a) adapalene-containing microspheres; and (b) clindamycin on a regular basis (e.g., once daily) for at least 12 weeks.

The present invention provides a method for inhibiting the recurrence of acne (e.g., acne vulgaris) in a mammal in which the clinical condition associated with the acne has been alleviated comprising applying to the afflicted skin region of the mammal the disclosed adapalene-containing microspheres and clindamycin fixed dose topical formulation.

Before application of topical microspheres formulation of the present invention onto the skin, the affected areas should be washed and dried and then the gel applied once daily, e.g., at bed time, wherein the eyes, lips and nose should be avoided. At first there may be a worsening of acne during the first few weeks of therapy because adapalene promotes the growth of pimples that have begun to form but are not yet visible. Therefore, treatment should not be stopped even if acne appears to be worsening. The beneficial effects could be seen after about 12 weeks therapy.

The efficacy safety and tolerability of the stable fixed dose topical formulation (Test formulation, Group B) of the present invention was evaluated vis-à-vis other formulations viz., 0.1% adapalene and 1% clindamycin gel (DERIVA® C, Group A), 1% Clindamycin gel (CLINDAC A®, Group C), 0.1% adapalene gel (ADAFERRIN®, Group D), and 0.1% microsphere adapalene gel (DERIVA® MS, Group E) over a period of 12 weeks in human patients (as described in Example 6). It was observed that the Test formulation (Group B) was more effective on reducing lesions' count when compared against other treatment groups. Group B also exhibited faster onset of action with trend towards reducing lesion count better than all the other groups. This effect points towards a better cumulative effect with microsphere adapalene and clindamycin in the treatment of acne.

It will be understood that various modifications may be made to the embodiments disclosed herein. Therefore the above description should not be construed as limiting, but merely as exemplifications of preferred embodiments. Other arrangements and methods may be implemented by those skilled in the art without departing from the scope and spirit of this invention.

All publications, patents, and patent applications cited in this application are herein incorporated by reference to the same extent as if each individual publication, patent, or patent application was specifically and individually indicated to be incorporated herein by reference.

The following examples are provided to enable one skilled in the art to practice the invention and are merely illustrative of the invention. The examples should not be read as limiting the scope of the invention.

EXAMPLES

Example 1

Preparation of Adapalene-Microspheres

| STEP | INGREDIENTS | Composition (gm/batch) |
| --- | --- | --- |
| I | Isopropyl alcohol | 0.8 liter |
|  | Methylene chloride | 2.8 liter |
| II | Adapalene | 10.0 |
| III | Plain microspheres (Ganz Pearl ® GMP 0820)* | 90.0 |

*Available from Ganz Chemical Company Ltd., Hyogo, Japan.

Into a 5.0 liter round bottom flask (RBF) was added 0.8 liter isopropyl alcohol and 2.8 liter methylene chloride. Then, 10.0 g adapalene was dissolved under stirring and 90.0 g plain microspheres were added with slow stifling. A simple distillation unit was set up, and distillation was begun.

| Initial temperature: 45° C. | RPM: 30 to 40 |
| --- | --- |

After 4 hours, the temperature was increased gradually as follows: 55° C., 60°, 70°, 80° C., 90° C., and to 100° C. When about 500 ml to 900 ml was left to distill, the contents of the RBF were transferred to 1 liter Bucchi® flask and evaporated to dryness in Bucchi® evaporator initially under low vacuum at 50° C. and then at high vacuum for at least 3 hours. The beads were dried at 60° C. under vacuum for 3 hours. The net weight was recorded.

Example 2

Fixed Dose Topical Gel Formulation of Clindamycin and Adapalene Microspheres

| Step | Ingredients | Composition (% w/w) |
| --- | --- | --- |
| I | Water | 67.255 |
|  | Disodium edetate | 0.050 |
|  | Carbomer ® 940 (CARBOPOL ® 940) | 0.550 |
| II | Water | 1.395 |
|  | Sodium hydroxide | 0.100 |
| III | Propylene glycol | 8.000 |
|  | Methylparaben | 0.100 |
|  | Poloxamer ® 407 (LUTROL ® F127) | 0.100 |
|  | Water | 2.000 |
|  | Phenoxyethanol | 0.250 |
|  | Adapalene microspheres (of EXAMPLE 1) (equivalent to Adapalene 0.1% w/w) | 1.000 |
| IV | Water | 18.00 |
|  | Clindamycin phosphate (equivalent to Clindamycin 1% w/w) | 1.200 |
|  | Total | 100 |

Manufacturing Process:

Step I. Carbomer Phase:

Into a stainless steel container, containing water, was dissolved disodium edetate. Carbomer®940 was slowly dispersed in small portions under stirring and allowed to soak for 1 hour.

Step II. Sodium Hydroxide Phase:

Sodium hydroxide was dissolved in water.

Step III. Gelling Phase:

The product of II was added to the product of I under stirring for 15 minutes to form a gel.

Step IV. Preservative and Adapalene Microspheres Phase:

Methylparaben was dissolved in propylene glycol at 50° C. to 55° C. Poloxamer®407 was added and dissolved in the solution. Water was added and the solution was cooled to 40° C. and then phenoxyethanol was added. Adapalene microspheres (prepared as per EXAMPLE 1) were dispersed slowly in small portions under stirring and stifling was continued for 10 minutes to form a uniform dispersion. The uniform dispersion was add to the main bulk (gel) passing through 100# sieve.

Step V. Clindamycin Phosphate Phase:

Clindamycin phosphate was dissolved in water and then added to the bulk in IV under stirring, and stifling was continued for 30 minutes.

Physical Parameters:

Description: white to off-white gel pH at 25° C.: 4.0 to 6.0

Example 3

Fixed Dose Topical Cream Formulation of Clindamycin and Adapalene Microspheres

| Step | Ingredients | Composition (% w/w) |
|---|---|---|
| I | Water | 58.150 |
|  | Disodium edetate | 0.050 |
|  | Glycerin | 5.000 |
|  | Carbomer ®934P (CARBOPOL ® 934P) | 0.550 |
| II | Methyl glucose sesquistearate (GLUCATE ® SS) | 1.000 |
|  | PEG-20 methyl glucose sesquistearate (GLUCATE SSE ®-20) | 1.500 |
|  | Cyclomethicone | 2.000 |
|  | Squalane | 3.000 |
|  | Methylparaben | 0.100 |
| III | Propylene glycol | 5.000 |
|  | Poloxamer ® 407 (LUTROL ® F127) | 0.100 |
|  | Water | 2.000 |
|  | Phenoxyethanol | 0.250 |
|  | Adapalene Microspheres (as per EXAMPLE 1) (equivalent to Adapalene 0.1% w/w) | 1.000 |
| IV | Water | 1.000 |
|  | Sodium hydroxide | 0.100 |
| V | Water | 18.00 |
| VI | Clindamycin phosphate (equivalent to Clindamycin 1% w/w) | 1.200 |
|  | Total | 100 |

Manufacturing Process:

Step I. Carbomer Phase (Aqueous Phase):
Into a stainless steel container containing water, was dissolved disodium edetate. Glycerin was added and then carbomer was dispersed slowly in small portions under stirring. The solution was allowed to soak for one hour and then was heated up to 70° C. to 72° C.

Step II. Oleaginous Phase:
Into a stainless steel container, II was added and then heated up to 70° C. to 72° C.

Step III. Emulsification:
The product of step II was added to the product of I at 70° C. to 72° C. and homogenized for 15 minutes and then allowed to cool under stirring.

Step IV. Sodium Hydroxide Phase:
Sodium hydroxide was dissolved in water and was added to the main bulk at 40° C.

Step V. Preservative and Adapalene, Microspheres Phase:
Methylparaben was dissolved in propylene glycol at 50° C. to 55° C. Poloxamer® 182 was added and dissolved. Water was added and allowed to cool to 40° C. Phenoxyethanol was then added. The adapalene microspheres (prepared as per EXAMPLE 1) were dispersed slowly in small portions under stifling and stirring was continued for 10 minutes to form a uniform dispersion. The uniform dispersion was added to the main bulk at 40° C. and passed through ASTM 100# sieve.

Step VI. Clindamycin Phosphate Phase:
Clindamycin phosphate was dissolved in water and then added to the bulk of V at 40° C. under stirring and stirring was continued for 30 minutes.

Physical Parameters:
Description: White to off-white cream
pH at 25° C.: 4.0 to 8.0

Example 4

Fixed Dose Topical Gel Formulation of Clindamycin and Adapalene Microspheres A. Incorporation of Adapalene in Plain Microspheres:

| Ingredients | Quantity |
|---|---|
| Adapalene | 1.0 g |
| Plain microspheres (Ganz Pearl ® GMP 0820) | 9.0 g |
| Tetrahydrofuran (THF) | 100.0 ml |

Adapalene was dissolved in THF. Into this solution, plain microspheres were dispersed and stirred for 60 min. THF was removed from the dispersion by distillation. After complete removal of THF, the dispersion was cooled to obtain adapalene loaded microspheres. These microspheres were washed with purified water (50 ml) and dried in a tray drier at about 40° C. to 60° C. till the loss on drying reaches less than 2% w/w. The dried microsphere were passed through ASTM #60 and #100 mesh, and stored in a triple laminated aluminum container until further use.

B. Preparation of Gel Composition Containing Microsphere Adapalene and Clindamycin:

| Step | Ingredients | Composition (% w/w) |
|---|---|---|
| I | Carbopol 980 | 1.10 |
|  | Purified water | 67.85 |
| II | Propylene glycol | 4.00 |
|  | Methyl paraben | 0.10 |
|  | Phenoxyethanol | 0.25 |
|  | Poloxamer ® 182 | 0.20 |
|  | Adapalene microspheres | 1.00 |
| III | Clindamycin Phosphate | 1.20 |
|  | Purified water | 20.00 |
| IV | Sodium hydroxide | 0.30 |
|  | Purified water | 4.00 |
|  | Total | 100.00 |

Manufacturing Process:
1. Carbopol®980 was slowly dispersed in water and allowed to soak for one hour.
2. Methyl paraben was dissolved in warm propylene glycol. Phenoxyethanol and Poloxamer®182 were added to it under stirring. Adapalene loaded microspheres (obtained above) were dispersed under stirring to obtain uniform dispersion.
3. Clindamycin phosphate was dissolved in water with stirring.
4. Sodium hydroxide was dissolved in water with stirring.
5. Sodium hydroxide solution was added to the Carbopol dispersion of 1 under gentle stirring and mixing to obtain gel.
6. Dispersion of 2 was added to the gel formed in 5.
7. Clindamycin solution of 3 was added to the gel of 6, and mixed well to form uniform gel.
8. pH of the gel formed in 7 was adjusted to 6.0 (range 5.4 to 6.2) by adding 10% sodium hydroxide solution.
9. The weight of the gel formed in 8 was adjusted to 100% by addition of water under stirring.

Physical Parameters:

Description: White to off-white gel pH: 6.0

C. Stability Data of Gel Composition Containing Microsphere Adapalene and Clindamycin:

Stability pack: Laminate tube with 12 μm barrier layer

Storage condition:

Temperature of about 40° C. and relative humidity of about 75%

Storage time: 3 months

| Test parameter | Stability data | |
|---|---|---|
| | Initial | After 3 months |
| Assay of adapalene (% w/w) | 103.4 | 101.7 |
| Assay of clindamycin phosphate (% w/w) | 101.8 | 93.0 |
| pH | 5.95 | 5.82 |
| Adapalene related impurities: (% w/w) | | |
| Single maximum impurity | 0.18 | 0.19 |
| Total impurities | 0.23 | 0.25 |
| Clindamycin phosphate related impurities: (% w/w) | | |
| Lincomycin HCL | 0.22 | 4.28 |
| Clindamycin base | 0.18 | 5.91 |
| Total impurities (excluding clindamycin base) | 0.79 | 5.05 |

Example 5

Effect of Varying pH on the Stability of Example 4 Composition

Eight replica batches (Batch A, B, C, D, E, F, G and H) of EXAMPLE 4 composition were prepared by the same process, except that the final pH of the corresponding compositions were adjusted to 4.5, 5.0, 5.4, 5.6, 5.8, 6.2, 6.4 and 6.5, respectively. These batches were packed in triple laminated aluminum container tubes, and were subjected to stability studies at temperature of about 40° C. and relative humidity of about 75% for 3 months.

The following are the stability data for these batches:

| | Stability data (40° C./75% RH) | | | | | | | |
|---|---|---|---|---|---|---|---|---|
| | Batch A (pH 4.5) | | Batch B (pH 5.0) | | Batch C (pH 5.4) | | Batch D (pH 5.6) | |
| Test Parameter | Initial | After 3 months | Initial | After 3 months | Initial | After 3 months | Initial | After 3 months |
| pH | 4.51 | 4.51 | 5.06 | 5.03 | 5.35 | 5.29 | 5.56 | 5.60 |
| Assay of clindamycin phosphate (% w/w) | 108.0 | 98.10 | 101.9 | 88.3 | 107.0 | 97.10 | 100.1 | 93.1 |
| Lincomycin impurity (% w/w) | 0.09 | 2.18 | 0.21 | 3.60 | 0.11 | 4.81 | 0.19 | 3.69 |
| Clindamycin base (% w/w) | 0.25 | 9.35 | 0.20 | 8.07 | 0.26 | 6.94 | 0.17 | 6.48 |
| Single maximum impurity* (% w/w) | 1.60 | 1.63 | 0.38 | 0.40 | 1.67 | 1.60 | 0.35 | 0.37 |
| Total impurities* (% w/w) (excluding clindamycin base) | 2.14 | 4.38 | 0.76 | 4.25 | 2.49 | 6.87 | 0.75 | 4.39 |

| | Stability data (40° C./75% RH) | | | | | | | |
|---|---|---|---|---|---|---|---|---|
| | Batch E (pH 5.8) | | Batch F (pH 6.2) | | Batch G (pH 6.4) | | Batch H (pH 6.5) | |
| Test Parameter | Initial | After 3 months | Initial | After 3 months | Initial | After 3 months | Initial | After 3 months |
| pH | 5.78 | 5.76 | 6.22 | 6.20 | 6.37 | 6.38 | 6.55 | 6.49 |
| Assay of clindamycin phosphate (% w/w) | 100.2 | 93.1 | 99.3 | 93.2 | 99.2 | 97.3 | 105.8 | 94.40 |
| Lincomycin impurity (% w/w) | 0.21 | 3.76 | 0.22 | 6.46 | 0.20 | 7.25 | 0.14 | 10.26 |
| Clindamycin base (% w/w) | 0.19 | 6.94 | 0.16 | 3.46 | 0.17 | 2.89 | 0.13 | 1.98 |
| Single maximum impurity* (% w/w) | 0.34 | 0.36 | 0.35 | 0.41 | 0.35 | 0.45 | 1.55 | 1.57 |
| Total impurities* (% w/w) (excluding clindamycin base) | 0.70 | 4.51 | 0.71 | 7.11 | 0.70 | 7.92 | 2.05 | 13.07 |

*Related to Clindamycin phosphate

Example 6

Efficacy, Safety, and Tolerability Study

A double-blind, randomized multi-center study is performed to evaluate the efficacy, safety and tolerability of a fixed dose gel of 0.1% w/w microsphere adapalene with 1% w/w clindamycin applied once daily and its effect in reducing the incidence of recurrence of acne vulgaris.

Study Objective

The objective of the study is to compare the efficacy, safety and tolerability of a fixed dose combination of 0.1% microsphere adapalene/1% clindamycin gel applied once daily (Treatment Group B: (Test Group)) to that of (1) 0.1% adapalene along with 1% clindamycin applied once daily (Treatment Group A), (2) 0.1% microsphere adapalene applied once daily, (Treatment Group E), (3) 1% clindamycin applied twice a day (Treatment Group C), and (4) 0.1% adapalene gel applied once daily (Treatment Group D); in reducing the incidence of the recurrence of acne in patients with mild to moderate acne vulgaris during the six month period following completion of the treatment.

Treatment Group A:

0.1% adapalene and 1% clindamycin gel (DERIVA® C, marketed by Glenmark Pharmaceuticals) is applied in the evening and placebo (gel) in the morning for 12 weeks.

Treatment Group B: (Test Group)

0.1% microsphere adapalene and 1% clindamycin gel in fixed dose combination (TEST FORMULATION) is applied in the evening and placebo (gel) in the morning for 12 weeks.

Treatment Group C:

1% Clindamycin gel (CLINDAC A, marketed by Galderma) is applied twice daily in the morning as well as the evening for 12 weeks.

Treatment Group D:

0.1% adapalene gel (ADAFERRIN, marketed by Galderma) is applied once daily in the evening and placebo in the morning for 12 weeks.

Treatment Group E:

0.1% microsphere adapalene gel (DERIVA® MS, marketed by Glenmark Pharmaceuticals) is applied once daily in the evening and placebo in the morning for 12 weeks Inclusion Criteria:

1. Males and non pregnant females.
2. Age: 13 to 30 years.
3. Mild to moderate facial acne vulgaris, with a defined minimum and maximum number of inflammatory lesions as per a standard scale.
4. Written informed consent by patient or parent/guardian in case of minor patient.

Method:

A prospective, multicentre, double blind, exploratory study conducted in 123 patients with a clinical diagnosis of mild to moderate acne. Total duration of study is 9 months, of which initial 3 months with active treatment and next 6 months follow up without any treatment to observe recurrence of acne. Intention to treat (ITT) analysis was done at end of $3^{rd}$ month treatment.

The study protocol, case record form and the patient information sheet were approved by the respective institutional review board. Patients fulfilling the selection criteria were assigned to one of the treatment group according to a randomization sheet, after obtaining their informed consent.

The efficacy variables on the Investigator's Global Assessment (IGA) and percent lesion reduction from baseline (total, inflammatory, and non-inflammatory). Lesion counts were assessed on the face only.

The efficacy parameters were assessed at baseline, and at the end of each visit. The following parameters were evaluated by Investigator: (i) Total Facial acne lesion count (inflammatory+non-inflammatory lesions); (ii) Inflammatory acne lesion count (papules, pustules, nodules) and iii) Non-inflammatory acne lesion count (open and closed comedones).

Results showed that at the end of 4 weeks of active treatment, there was a faster improvement in IGA score in Treatment Group B over Treatment Group A IGA scores based on FDA acne grading scale (see Table 1 below), measured at the end of the treatment and at each follow up visit.

TABLE 1

Investigator's Global Assessment ("IGA") Score Description

| Grade | Description |
|---|---|
| 0 | Clear skin with no inflammatory lesions or non inflammatory lesions |
| 1 | Almost clear; few non-inflammatory lesions with not more than one or two small inflammatory lesions. |
| 2 | Mild severity; greater than Grade 1; some non-inflammatory lesions with no more than a few inflammatory lesions (papules/pustules only, no nodular lesions) |
| 3 | Moderate severity; greater than Grade 2; up to many non-inflammatory lesions and may have some inflammatory lesions, but no more than two small nodular lesion. |
| 4 | Severe; greater than Grade 3; up to many non-inflammatory and inflammatory lesions, but no more than a few nodular lesions. |

| Assessment Score | Group A (N = 23) | | Group B (N = 25) | | Group C (N = 24) | | Group D (N = 25) | | Group E (N = 26) | |
|---|---|---|---|---|---|---|---|---|---|---|
| | No | % | No | % | No | % | No | % | No | % |
| 0 | — | — | 01 | 04.0 | — | — | — | — | — | — |
| 1 | 01 | 04.4 | 03 | 12.0 | — | — | — | — | — | — |
| 2 | 06 | 26.0 | 11 | 44.0 | 03 | 12.5 | 03 | 12.0 | 04 | 15.4 |
| 3 | 12 | 52.2 | 07 | 28.0 | 16 | 66.7 | 15 | 60.0 | 17 | 65.4 |
| 4 | 04 | 17.4 | 03 | 12.0 | 05 | 20.8 | 07 | 28.0 | 05 | 19.2 |

| Demographical Data | | | | | |
|---|---|---|---|---|---|
| Parameters | Group A | Group B | Group C | Group D | Group E |
| No. of patients @ Age (yrs) | 23 | 25 | 25 | 24 | 26 |
| Mean | 20.87 | 20.50 | 20.77 | 21.18 | 19.17 |
| SD | 4.21 | 3.72 | 3.70 | 4.10 | 5.51 |
| Range | 15-32 yrs | 14-29 yrs | 15-29 yrs | 16-32 yrs | 15-30 yrs |

-continued

Demographical Data

| Parameters | Group A | Group B | Group C | Group D | Group E |
|---|---|---|---|---|---|
| @ Weight (kg) | | | | | |
| Mean | 57.71 | 53.06 | 55.63 | 55.13 | 51.59 |
| SD | 11.90 | 9.77 | 12.08 | 10.51 | 10.31 |
| Range | 45-87 kg | 40-70 kg | 40-74 kg | 40-72 kg | 37-80 kg |
| @ Height (cm) | | | | | |
| Mean | 168.86 | 152.11 | 166.50 | 163.78 | 161.22 |
| SD | 6.54 | 25.62 | 11.28 | 8.70 | 9.01 |
| Range | 158-176 cm | 87-174 cm | 146-179 cm | 152-179 cm | 152-178 cm |
| # Sex (%) | | | | | |
| Male | 13 (56.52) | 11 (44.00) | 13 (52.00) | 15 (62.50) | 14 (53.85) |
| Female | 10 (43.48) | 14 (56.00) | 12 (48.00) | 09 (37.50) | 12 (46.15) |

@ By ANOVA
P > 0.05 Not Significant
By Chi - Square Test

COMPARISON OF CHANGES IN MEAN PAPULES

| Duration in | No. of Papules (Mean ± SD) | | | | |
|---|---|---|---|---|---|
| Weeks | Group A | Group B | Group C | Group D | Group E |
| Baseline | 16.59 ± 8.71 | 16.42 ± 5.35 | 14.60 ± 7.72 | 17.40 ± 8.54 | 16.15 ± 8.24 |
| 4 | *12.64 ± 10.38 | *10.91 ± 5.43 | 12.99 ± 7.02 | 15.08 ± 8.02 | 14.16 ± 4.74 |
| (% Change) | (23.81) | (33.56) | (11.03) | (13.34) | (12.32) |
| 8 | *6.20 ± 4.22 | *5.95 ± 4.02 | @*7.96 ± 5.60 | @*9.48 ± 5.64 | @*8.56 ± 4.89 |
| (% Change) | (62.63) | (63.76) | (45.48) | (45.52) | (47.00) |
| 12 | *5.08 ± 3.61 | *4.23 ± 3.68 | @*6.36 ± 5.27 | @*7.95 ± 6.16 | @*6.01 ± 2.81 |
| (% Change) | (69.38) | (74.24) | (56.44) | (54.31) | (62.79) |

By ANOVA
*P < 0.05, Significant
@Between Groups
P < 0.05, Significant

COMPARISON OF CHANGES IN MEAN TOTAL INFLAMMATORY LESION

| Duration in | No. of Inflammatory Lesion (Mean ± SD) | | | | |
|---|---|---|---|---|---|
| Weeks | Group A | Group B | Group C | Group D | Group E |
| Baseline | 22.18 ± 9.37 | 21.47 ± 7.47 | 20.42 ± 11.05 | 23.56 ± 10.25 | 21.78 ± 8.24 |
| 4 | *16.25 ± 10.54 | *13.71 ± 7.41 | @*17.22 ± 8.95 | @*19.78 ± 8.90 | @*18.23 ± 5.73 |
| (% Change) | (26.23) | (36.14) | (15.67) | (16.04) | (16.30) |
| 8 | *8.31 ± 7.57 | *7.60 ± 5.06 | @*11.04 ± 7.02 | @*13.29 ± 7.00 | @*11.61 ± 6.35 |
| (% Change) | (63.34) | (64.60) | (45.93) | (43.59) | (46.69) |
| 12 | *6.01 ± 4.32 | *4.85 ± 4.02 | @*9.09 ± 5.26 | @*11.04 ± 7.13 | @*8.71 ± 4.97 |
| (% Change) | (72.90) | (77.41) | (55.48) | (53.14) | (60.00) |

By ANOVA
*P < 0.05, Significant
@ Between Groups
P < 0.05, Significant

COMPARISON OF CHANGES IN MEAN TOTAL NON-INFLAMMATORY LESION

| Duration in | No. of Non-Inflammatory Lesion (Mean ± SD) | | | | |
|---|---|---|---|---|---|
| Weeks | Group A | Group B | Group C | Group D | Group E |
| Baseline | 20.79 ± 12.46 | 18.08 ± 8.49 | 18.46 ± 10.66 | 20.97 ± 9.94 | 19.21 ± 9.38 |
| 4 | *16.58 ± 11.72 | @*12.24 ± 8.1 | @16.49 ± 7.59 | @18.85 ± 7.07 | @17.06 ± 11.40 |
| (% Change) | (20.25) | (32.30) | (10.67) | (10.11) | (11.19) |

COMPARISON OF CHANGES IN MEAN TOTAL NON-INFLAMMATORY LESION

| Duration in | No. of Non-Inflammatory Lesion (Mean ± SD) | | | | |
|---|---|---|---|---|---|
| Weeks | Group A | Group B | Group C | Group D | Group E |
| 8 | *11.02 ± 7.22 | *8.00 ± 8.09 | @*13.42 ± 7.59 | @*16.09 ± 5.79 | @*13.11 ± 8.52 |
| (% Change) | (46.99) | (55.75) | (27.30) | (23.27) | (31.75) |
| 12 | *8.00 ± 6.59 | *6.50 ± 6.39 | @*10.21 ± 6.55 | @*12.02 ± 6.47 | @*10.49 ± 10.0 |
| (% Change) | (61.52) | (64.05) | (44.69) | (42.68) | (45.39) |

By ANOVA
*P < 0.05, Significant
@Between Groups
P < 0.05, Significant

COMPARISON OF CHANGES IN MEAN TOTAL LESION

| Duration in | No. of Total Lesion (Mean ± SD) | | | | |
|---|---|---|---|---|---|
| Weeks | Group A | Group B | Group C | Group D | Group E |
| Baseline | 42.97 ± 21.78 | 39.55 ± 14.90 | 38.88 ± 19.75 | 44.53 ± 16.37 | 40.99 ± 16.18 |
| 4 | *33.23 ± 20.5 | @*25.95 ± 13.3 | 32.71 ± 15.51 | 37.63 ± 12.28 | 34.29 ± 15.62 |
| (% Change) | (22.67) | (34.39) | (15.87) | (15.50) | (16.35) |
| 8 | *19.33 ± 13.4 | *15.60 ± 9.70 | @*24.46 ± 13.4 | @*29.38 ± 10.0 | @*24.72 ± 13.1 |
| (% Change) | (55.02) | (60.56) | (37.09) | (34.03) | (39.69) |
| 12 | *14.01 ± 9.17 | *11.35 ± 8.08 | @*19.30 ± 11.0 | @*23.06 ± 10.2 | @*19.20 ± 12.1 |
| (% Change) | (67.40) | (71.30) | (50.36) | (48.21) | (53.16) |

By ANOVA
*P < 0.05, Significant
@Between Groups
P < 0.05, Significant

From the results of the effects of various treatments on inflammatory lesions and total lesion count as described in the tables above, it is apparent that Group B (Test formulation group) is more effective on reducing the count of lesions when compared against other treatment groups. It is also evident that there is a faster onset of action in Group B with a trend towards reducing lesion counts better than all the other groups. Cumulatively, the effects show a better effect with microsphere adapalene and clindamycin in the treatment of acne.

Safety Endpoints:

Safety is assessed by comparing the severity and frequency of adverse events (erythema, scaling, stinging/burning, and itching and dryness) in all the treatment groups, inclusive of any other local and systemic adverse events, which were recorded within the duration of the nine month study.

| Events | Group A (N = 23) | | Group B (N = 25) | | Group C (N = 25) | | Group D (N = 24) | | Group E (N = 26) | |
|---|---|---|---|---|---|---|---|---|---|---|
| | No | % | No | % | No | % | No | % | No | % |
| Burning | 07 | *30.4 | 01 | 04.00 | 01 | 04.00 | 09 | 37.5 | 04 | 15.4 |
| Dryness | 01 | 04.3 | 01 | 04.00 | 02 | 08.00 | 01 | 04.2 | — | — |
| Irritation | 03 | 13.0 | 01 | 04.00 | 01 | 04.3 | 02 | 08.3 | 02 | 04.3 |
| Scaling | — | — | 01 | 04.00 | — | — | — | — | — | — |
| No of patients | 11 | *47.7 | 04 | 16.00 | 04 | 16.00 | 12 | 50 | 06 | 23.1 |

By Chi Square Test
*P < 0.05 Significant

Example 7

Efficacy Study for Reduction of Incidence of Recurrence of Acne Vulgaris

Evaluation of efficacy of a fixed dose combination of 0.1% microsphere adapalene/1% clindamycin gel applied once daily (Treatment Group B: (Test Group)) to that of (1) 0.1% adapalene along with 1% clindamycin applied once daily (Treatment Group A), (2) 0.1% microsphere adapalene applied once daily, (Treatment Group E), (3) 1% clindamycin applied twice a day (Treatment Group C), and (4) 0.1% adapalene gel applied once daily (Treatment Group D) in reduction of incidence of recurrence of acne vulgaris

| | Profile of Recurrence Rates | | |
|---|---|---|---|
| | No. of patients followed up for | Recurrence rate (>50%) increase in the lesions | |
| Treatment Groups | 6 months | Number | % |
| Group A | 23 | 05 | 21.7 |
| Group B (Test Group) | 25 | Nil | — |
| Group C | 24 | 07 | 29.2 |
| Group D | 25 | 08 | 32.0 |
| Group E | 26 | 06 | 23.1 |

The active treatment was administered to various groups above for 12 weeks and patients were subsequently followed up for a period of 3 months—an observation period to see recurrence in total number of acne lesions (which included inflammatory as well as non-inflammatory lesions). Recurrence was defined as a 50% increase in the number of lesions from the baseline taken at the end of 12 weeks treatment. As per the follow-up of these groups, it is clear from the table above that the lowest recurrence rate reported was in the Group B (Test Group) which was nil.

It will be understood that various modifications may be made to the embodiments disclosed herein. Therefore the above description should not be construed as limiting, but merely as exemplifications of preferred embodiments. For example, the functions described above and implemented for operating the present invention are for illustration purposes only. Other arrangements and methods may be implemented by those skilled in the art without departing from the scope and spirit of this invention.

We claim:

1. A stable fixed dose topical formulation having a pH in the range of 5.4 to 6.2 comprising from about 0.01% to about 0.3% by weight of adapalene contained in methacrylate based polymer microspheres, free of vinylpyridine derivative; and from about 0.5% to about 5.0% by weight of clindamycin, where the clindamycin is in the form of clindamycin phosphate.

2. The formulation of claim 1, which is storage stable at a temperature of about 40° C. and relative humidity of about 75% for a period of at least 3 months.

3. The formulation of claim 1, wherein the microspheres have a mean particle size ranging from about 2 μm to about 30 μm.

4. The formulation of claim 1, wherein the formulation is in the form of a gel, lotion, paste, dispersion, ointment or cream.

5. A stable fixed dose topical gel formulation having a pH in the range of 5.4 to 6.2 comprising: (a) 0.1% w/w of adapalene; (b) 1.0% w/w of clindamycin; and (c) a gelling agent, wherein the adapalene is contained in methacrylate based polymer microspheres, free of vinylpyridine derivative and where the clindamycin is in the form of clindamycin phosphate.

6. The formulation of claim 5, wherein the gelling agent is about 0.5% to about 1.5% by weight carbomer.

7. The formulation of claim 5, which is storage stable at a temperature of about 40° C. and relative humidity of about 75% for a period of at least 3 months.

8. The formulation of claim 5, wherein the microspheres have a mean particle size ranging from about 2 μm to about 30 μm.

9. A method of treating acne or reducing the recurrence of acne in a mammal in need thereof comprising applying to the afflicted skin region of the mammal the formulation of claim 5.

* * * * *